(12) United States Patent
Korycinska et al.

(10) Patent No.: US 7,057,041 B2
(45) Date of Patent: Jun. 6, 2006

(54) PROCESS FOR THE PREPARATION OF ZALEPLON

(76) Inventors: Monika Korycinska, ul. Okinskiego 6 m. 59, 02-115 Warsaw (PL); Tomasz Stawinski, Dzlechciniec 5B, 05-462 Wiazowna (PL); Maciej Wieczorek, ul. Majowa 20, 05-462 Lomianki (PL)

( * ) Notice: Subject to any disclaimer, the term of this patent is extended or adjusted under 35 U.S.C. 154(b) by 0 days.

(21) Appl. No.: 10/514,045

(22) PCT Filed: May 12, 2003

(86) PCT No.: PCT/PL03/00043

§ 371 (c)(1), (2), (4) Date: May 17, 2005

(87) PCT Pub. No.: WO03/095456

PCT Pub. Date: Nov. 20, 2003

(65) Prior Publication Data

US 2005/0234237 A1    Oct. 20, 2005

(30) Foreign Application Priority Data

May 14, 2002 (PL) .................................. 353870

(51) Int. Cl.
*C07D 487/04* (2006.01)
(52) U.S. Cl. ...................................................... 544/281
(58) Field of Classification Search ................. 544/281
See application file for complete search history.

(56) References Cited

U.S. PATENT DOCUMENTS 5,714,607 A * 2/1998 Padmanathan ............... 544/281
6,884,888 B1 * 4/2005 Korodi et al. ............... 544/281

* cited by examiner

*Primary Examiner*—Shailendra Kumar

(57) ABSTRACT

The invention relates to a process for the preparation of zaleplon (N-[3(3-cyanopyrazolo[1,5-a]pyrim-idin-7-yl)phenyl]-N-ethyl-accramide) in the reaction of 3-dimethylamino-1-(3-N-ethyl-N-acetylamirnophenyl)-2-propen-1-one with 3-aminopyrazole-4-carbonitrile, which comprises carrying out said reaction in an aqueous solution of formic acid at formic acid concentrations in the range of 20–80% (w/w). Zaleplon is useful as an anxiolytic, a sedactive and a skeletal muscle relaxant.

6 Claims, No Drawings

PROCESS FOR THE PREPARATION OF ZALEPLON

This application is a 371 of PCT/PL03/00043, filed May 12, 2003.

The invention relates to the field of the synthesis of N-[3-(3-cyanopyrazolo[1,5-a]pyrimidin-7-yl)phenyl]-N-ethylacetamide (zaleplon), useful in medicine as an anxiolytic, sedative and skeletal muscle relaxing agent.

Patents EP 0776898 and EP 0208846 describe a process for the preparation of zaleplon, which consists in reaction of 3-dimethylamino-1-(3-N-ethyl-N-acetylaminophenyl)-2-propen-1-one with 3-aminopyrazole-4-carbonitrile, by heating in acetic acid (EP 0208846) or in an aqueous solution of acetic acid (EP 0776898). According to the teachings of EP 0776898, carrying out the reaction in aqueous acetic acid would make it possible to obtain the product free from color impurities, in a much higher yield (ca. 90%) and of much better purity (above 98.77%), compared to the reaction carried out in neat acetic acid. Such improved approach would also allow one to shorten the reaction time and to lower the reaction temperature.

However, the present inventors have found that the reaction carried out under conditions described in EP 0776898, invariably resulted in zaleplon contaminated with a side product, N-[3-(3-cyanopyrazolo[1,5-a]pyrimidin-5-yl)phenyl]-N-ethylacetamide, which for the purpose of the present description is called "the isomer". The yield of this "isomer", depending on the reaction parameters, is in the range of 10–20%.

The present inventors have isolated "the isomer" from the reaction mixture and, in order to verify the structure, analyzed it by the usual spectroscopic methods, such as IR, $^1$H-NMR, $^{13}$C-NMR, MS, UV and elemental analysis (IR (KBr): (cm$^{-1}$) 3436,8, 3103,8, 3065,1, 2977,1, 2937,1, 2228,1, 1656,6, 1625,4, 1602,4, 1602,1, 1553,9, 1521,8, 1469,1, 1412,1, 1302,7, 1280,1, 1221,5, 1189,0, 1142,9, 1088,1, 1004,6, 900,1): UV (c=0,01042 mg/ml in MeOH, nm): 301,00 (0,3082), 261,20 (1,1743), 219,20 (0,9612), 216,20 (0,9618). It has also been determined (using a differential scanning calorimeter) that the compound melts in the temperature range of 204–207° C., while the melting range for zaleplon is 185–188° C.

None of the prior art documents cited above mentions of the formation of the side product, N-[3-(3-cyanopyrazolo[1,5-a]-pyrimidin-5-yl)phenyl]-N-ethylacetamide. Nevertheless, the formation of this by-product creates a serious technological problem in the industrial scale production of zaleplon intended for use as an active ingredient in pharmaceutical formulations.

According to current standards, the allowed level of a single identified and qualified drug impurity, such as "the isomer", should be no more than 0.5% (wt/wt), or 20 micrograms of the total daily dose. Due to a high degree of structural and chemical similarity between zaleplon and "the isomer" these compounds are very difficult to separate by standard crystallization methods, particularly when the content of the isomer is above 10%. Moreover, the multiple crystallization necessary in such cases causes substantial losses of the desired active ingredient, zaleplon. Crude zaleplon may be crystallized from a polar solvent chosen from lower alkyl alcohols, such as methanol, ethanol and isopropanol. The presence of impurities, such as "isomer", necessitates additional crystallization from a less polar solvent, e.g. chosen from among esters, such as ethyl acetate, butyl acetate, or similar. Thus, the methods known from the prior art do not allow to obtain the final product of required quality, in a simple way.

The present inventors have undertaken an investigation of a solution of this problem by changing the reaction conditions, including changes to the reaction medium. Attempts to find appropriate conditions in aqueous acetic acid did not result in decreased amounts of the isomer, similarly as in propionic acid solutions. However, the authors have unexpectedly found that the formation of such substantial amounts of the isomer can be avoided if the reaction is carried out in aqueous formic acid medium.

Thus, the present invention relates to the process for the preparation of zaleplon, N-[3-(3-cyanopyrazolo[1,5-a]pyrimidin-7-yl)phenyl]-N-ethylacetamnide 3, in the reaction of 3-dimethylamino-1-(3-N-ethyl-N-acetylaminophenyl)-2-propen-1-one 1 with 3-aminopyrazole-4-carbonitrile 2, which comprises carrying out the reaction in an aqueous solution of formic acid, at concentrations of formic acid in the range of 20–80% (wt/wt), according to the Scheme presented below. Isomer 4 is formed with a very low yield.

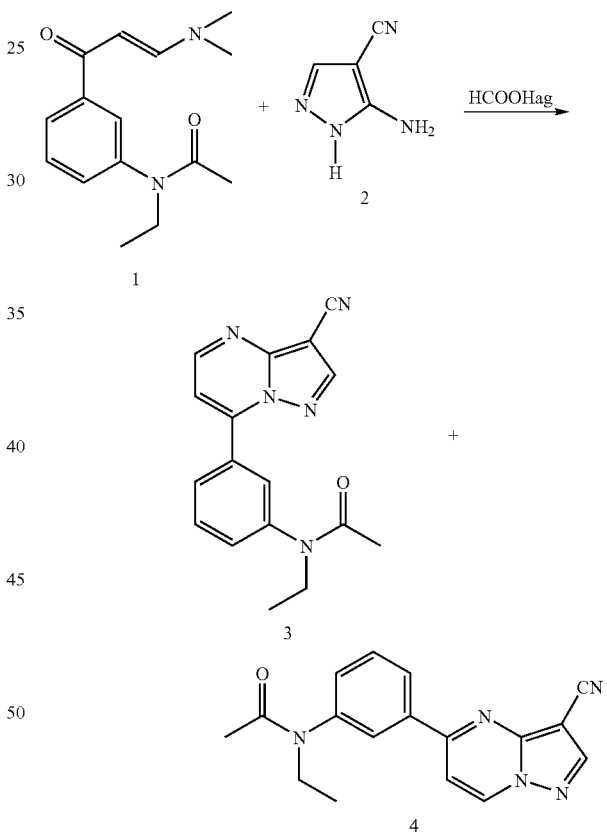

The reaction is carried out by stirring the reaction mixture at temperatures in the range of 20–60° C., preferably at 30–45° C. After the reaction is complete, the reaction optionally is diluted with water to give formic acid concentration below 40% (wt/wt), which causes zaleplon crystals to precipitate.

Preferably, a 35–45% (wt/wt) solution of formic acid is used.

The low content of the isomer present in the crude zaleplon obtained from the reaction makes possible easy purification of zaleplon to purity levels in accordance with the standard requirements established for pharmaceutical active ingredients. Moreover, the yield of the reaction carried out according to the present invention is increased by a few percent compared to the process described in EP 0776898.

Isolating the product from the reaction mixture after completion of the reaction results in crude zaleplon of high purity. It can be additionaly crystallized from a polar solvent chosen from lower alkyl alcohols, e.g. from methanol, ethanol or isopropanol, or from a less polar solvent, e.g. belonging to the ester group, such as ethyl acetate, butyl acetate, or similar. When required, additional crystallization can be carried out. However, generally one crystallization affords zaleplon of sufficient purity.

When carrying the reaction according to the present process, usually one crystallization of crude zaleplon is sufficient. However, if necessary, it is possible to recrystallize zaleplon from a less polar solvent e.g. belonging to the ester group, such as ethyl acetate, butyl acetate or the like.

The zaleplon obtained by the process of the present invention, after one crystallization contains "the isomer" in the amount of less than 5 micrograms per dosage unit containing 10 mg zaleplon.

The present invention will now be described with reference to the following specific, illustrative and non-limiting embodiments.

EXAMPLE 1

Preparation of Crude Zaleplon

3-Dimethylamino-1-(3-N-ethyl-N-acetylaininophenyl)-2-propen-1-one (1) (104.14 g, 0.4 mol), 3-aminopyrazole-4-carbonitrile (2) (44.32 g, 0.41 mol) and 35% aqueous formic acid (1360 mL, 1500 g) are placed in a reactor. The mixture is stirred (ca. 200 rpm) and slowly warmed up to 35° C. over 1 hr. Then the mixture is warmed up to 40° C. over 30 minutes and stirred at 40° C. one more hour (total heating time is 2.5 hr from the beginning of heating). Subsequently, the mixture is cooled to ca. 10° C. and stirred at this temperature for ca. 30 minutes. Then it is filtered, the precipitate is thoroughly pressed and washed with water (3×250mL). The precipitate—white to off-white crystals—is dried at 105° C. The yield is 87.5% (106.86 g). The purity of the crude product is 99.69% as determined by HPLC.

EXAMPLE 2

Crystallization of Crude Zaleplon

Crude zaleplon obtained in the above Example 1 is placed in a reactor equipped with a stirrer, methanol (8:1, v/w) is added and the mixture is heated to reflux (temperature ca. 65° C.). After the crystals completely dissolved, stirring is continued under reflux for another 20–30 minutes. Then the solution is cooled to 10° C. and stirred at this temperature for 2 hours, until all the product crystallized. The precipitate is separated from the mother liquor under reduced pressure, washed with methanol (5° C., 1×250 ml), thoroughly pressed and dried at 80° C. Yield of crystallization: 90%. Purity of the product (as determined by HPLC): 99.98%.

EXAMPLE 3 (COMPARATIVE)

A comparative study of the processes for zaleplon preparation was conducted, using as the reaction medium aqueous solutions of formic acid (according to the present invention), acetic acid (prior art) and propionic acid (as reference), at various acid concentrations.

The selectivity of these reactions was assayed by HPLC (C 18, Luna 250×5 mm column; mobile phase: pH 6.8 buffer-acetonitrile mixture, 2:1 v/v; a Waters chromatograph with a PDD detector). The results are summarized in the Table below.

| Acid | Acid concentration | Selectivity (%) (HPLC) | | Yield of zaleplon |
|---|---|---|---|---|
| | | Zaleplon 3 | Isomer 4 | |
| HCOOH | 35 | 99.69 | 0.09 | 87% |
| | 45 | 99.82 | 0.06 | 86% |
| | 55 | 99.81 | 0.00 | 86% |
| CH₃COOH | 45 | 49.87 | 13.24 | 58% |
| | 60 | 65.34 | 11.24 | 62% |
| | 80 | 98.05 | 1.86 | 68% |
| CH₃CH₂COOH | 35 | 49.27 | 9.60 | 42% |
| | 45 | 49.56 | 9.58 | 44% |
| | 60 | 45.00 | 12.70 | 47% |
| | 80 | 51.30 | 12.70 | 53% |
| | 99 | 22.10 | 12.92 | 34% |

As it can be seen from the above Table, by replacing acetic acid with its higher homologue-propionic acid, the formation of the undesirable isomer is not voided. However, by running the reaction in formic acid solutions the desired product is obtained practically free from the isomer.

EXAMPLE 4

Crystallization of Crude Zalepon in a Large Scale

Technical zalepon (5 kg) is placed in a reactor equipped with a stirrer, 40 l of methanol as added and the mixture is heated to reflux and maintained under these conditions until all the product dissolves (ca 30 min.) Then the solution while still hot is filtered through candle filter to remove mechanical impurities and obtained clear solution is cooled to 10° C. and stirred at this temperature for 2 hours. Precipitated solid is filtered under reduced pressure, washed with cold (5° C.) methanol (2×500 ml) and dried in a shelf dryer at 80° C. 4.52 kg pure product is obtained (yield of crystallization: 90%). Purity of the product (as determined by HPLC): 99.98%.

The invention claimed is:

1. A process for the preparation of zaleplon (N-[3-(3-cyano-pyrazolo[1,5-a]pyrimidin-7-yl)phenyl]-N-ethylacetamide), said process comprising:
    reacting 3-dimethylamino-1-(3-N-ethyl-N-acetylaminophenyl)-2-propen-1-one with 3-aminopyrazole-4-carbonitrile,
    wherein the reaction is carried out in an aqueous solution of formic acid, at formic acid concentrations in the range of 20–80% (w/w).

2. The process of claim 1, wherein the concentration of said formic acid solution is in the range of 35–45% (w/w).

3. The process of claim 1, wherein after the reaction is completed, the reaction mixture is diluted with water to achieve a concentration of formic acid below 40% (w/w).

4. The process of claim 1, further comprising crystallization of crude zaleplon.

5. The process of claim 4, wherein the crystallization of crude zaleplon is from a lower alkyl alcohol selected from the group consisting of methanol, ethanol and isopropanol.

6. The process of claim 4, wherein the crystallization of crude zaleplon is from a lower organic ester selected from the group consisting of ethyl acetate and butyl acetate.

* * * * *